(12) United States Patent
Gorovoy

(10) Patent No.: US 10,179,059 B1
(45) Date of Patent: Jan. 15, 2019

(54) ORAL APPLIANCE FOR APPETITE SUPPRESSION

(71) Applicant: Shahla Gorovoy, Harriman, NY (US)

(72) Inventor: Shahla Gorovoy, Harriman, NY (US)

( * ) Notice: Subject to any disclaimer, the term of this patent is extended or adjusted under 35 U.S.C. 154(b) by 476 days.

(21) Appl. No.: 15/150,906

(22) Filed: May 10, 2016

(51) Int. Cl.
*A61F 5/00* (2006.01)
*A61F 5/37* (2006.01)
*A61C 17/00* (2006.01)

(52) U.S. Cl.
CPC ................... *A61F 5/0006* (2013.01)

(58) Field of Classification Search
CPC ..................................................... A61F 5/0006
USPC ................. 433/18, 23, 19, 215, 6, 9, 25, 80; 128/897, 848, 898; 600/300, 23, 24; 434/127, 262, 263; 601/38
See application file for complete search history.

(56) References Cited

U.S. PATENT DOCUMENTS

| | | | |
|---|---|---|---|
| 4,471,771 A | 9/1984 | Brown | |
| 4,727,867 A | 3/1988 | Knoderer | |
| 5,924,422 A | 7/1999 | Gustafson | |
| 5,979,449 A | 11/1999 | Steer | |
| D548,402 S | 8/2007 | Trodick | |
| 8,375,954 B2* | 2/2013 | Pines | A61F 5/0006 128/846 |
| 9,180,034 B1* | 11/2015 | Kapil | A61F 5/0006 |
| 2003/0075186 A1* | 4/2003 | Florman | A61C 7/36 128/869 |
| 2010/0034860 A1 | 2/2010 | Bardach | |
| 2010/0105001 A1* | 4/2010 | Bulloch | A61C 7/22 433/18 |
| 2010/0288287 A1* | 11/2010 | Pines | A61F 5/0006 128/846 |
| 2014/0283849 A1* | 9/2014 | Pecina | A61C 7/36 128/869 |
| 2015/0034097 A1* | 2/2015 | Pines | A61F 5/0006 128/859 |

FOREIGN PATENT DOCUMENTS

WO   WO2013136178 A2   9/2013

* cited by examiner

*Primary Examiner* — Tarla R Patel
(74) *Attorney, Agent, or Firm* — Kyle A. Fletcher, Esq.

(57) ABSTRACT

The oral appliance for appetite suppression is a device that limits the range of motion of the mouth which prevents impulse eating. In one potential embodiment of the disclosure the oral appliance of appetite suppression comprises an upper molar clip, a lower molar clip, and an elastic band.

17 Claims, 4 Drawing Sheets

ORAL APPLIANCE FOR APPETITE SUPPRESSION

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

The present invention relates to the field of dental devices and orthodontic devices, more specifically, an intraoral device designed to limit the opening of the mouth.

The weight control and weight loss methods have been a national obsession for decades. While many methods exist to help people with their weight control, one of the oldest and most effective methods remains reducing the caloric intake of the individual.

One effective, though unfortunate, way to reduce caloric intake is injury to the mouth. Put frankly, when difficult to move the mouth, people eat less.

SUMMARY OF INVENTION

Therefore, one potential weight loss strategy is to limit the motion of the mouth so that it is more difficult to eat. The oral appliance for appetite suppression is a device that limits the range of motion of the mouth, which prevents impulse eating. In one potential embodiment of the disclosure the oral appliance for appetite suppression comprises an upper molar clip, a lower molar clip, and an elastic band. The elastic band is affixed to both the upper molar clip and the lower molar clip in order to adaptively limit the ability to open one's mouth.

These together with additional objects, features and advantages of the oral appliance for appetite suppression will be readily apparent to those of ordinary skill in the art upon reading the following detailed description of the presently preferred, but nonetheless illustrative, embodiments when taken in conjunction with the accompanying drawings.

In this respect, before explaining the current embodiments of the oral appliance for appetite suppression in detail, it is to be understood that the oral appliance for appetite suppression is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the oral appliance for appetite suppression.

It is therefore important that the claims be regarded as including such equivalent construction insofar as they do not depart from the spirit and scope of the oral appliance for appetite suppression. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

Figure 1:
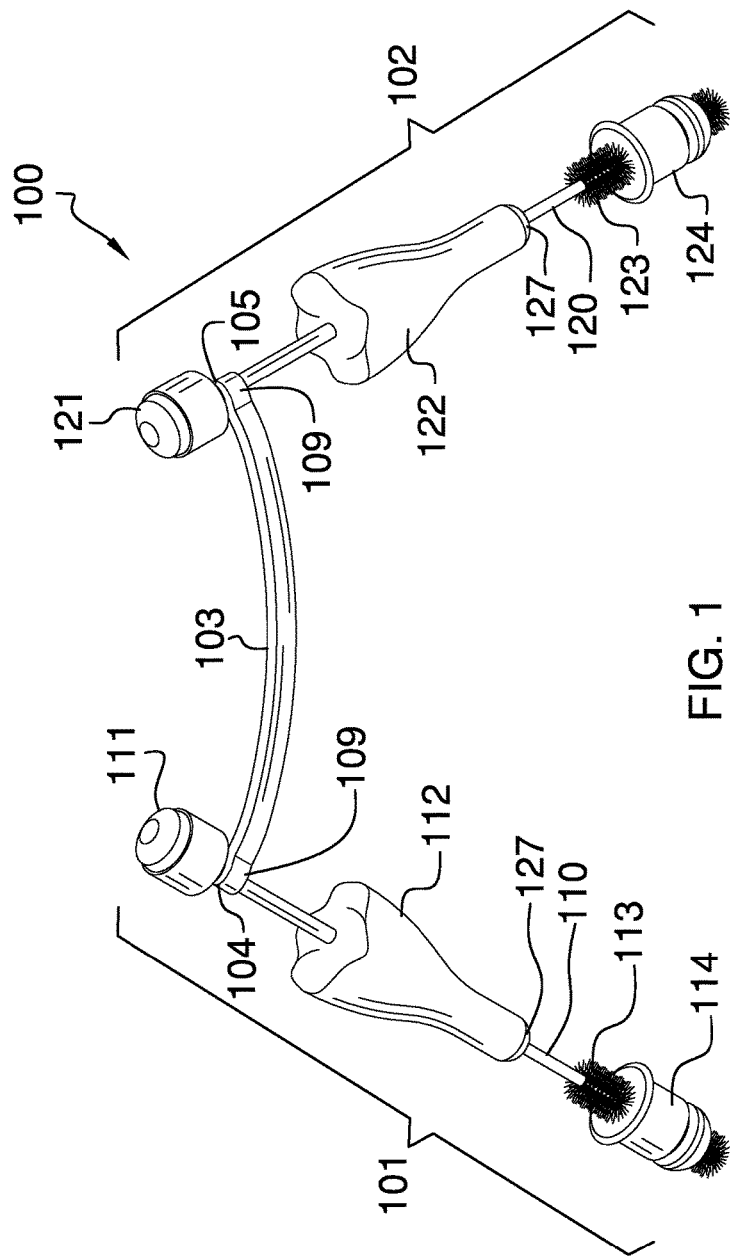
FIG. 1 is a perspective view of an embodiment of the disclosure.
Figure 2:
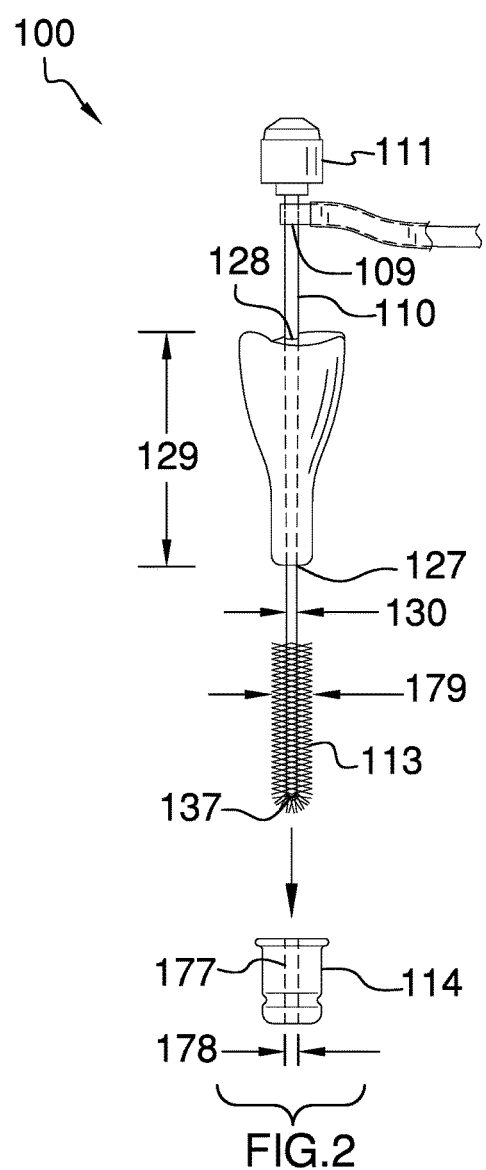
FIG. 2 is a side view of an embodiment of the disclosure.

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Detailed reference will now be made to a first potential embodiment of the disclosure, which is illustrated in FIGS. 1 through 4.

The oral appliance for appetite suppression 100 (hereinafter invention) comprises an upper molar clip 101, a lower molar clip 102, and an elastic connector 103. The elastic connector 103 has a first end 104 and a second end 105. The upper molar clip 101 is attached to the first end 104 of the elastic connector 103 and the lower molar clip 103 is attached to the second end 105 of the elastic connector 103. The elastic connector 103 provides resistance when opening a mouth of an end user.

The upper molar clip 101 is identical to the lower molar clip 102. The upper molar clip 102 is further defined with an upper bar member 110. The upper bar member 110 includes a fixed upper cap 111, an upper intermediate member 112, an upper brush member 113, and an upper securing cap 114.

The lower molar clip 103 is further defined with a lower bar member 120. The lower bar member 120 includes a fixed lower cap 121, a lower intermediate member 122, a lower brush member 123, and a lower securing cap 124.

The elastic connector 103 includes a loop 109 at the first end 104 and at the second end 105. The loop 109 at the first end 104 of the elastic connector 103 is affixed to the upper bar member 110; whereas the loop 109 at the second end 105 of the elastic connector 103 is affixed to the lower bar member 120. The loop 109 of the first end 104 of the elastic connector 103 is sandwiched between the upper intermediate member 112 and the fixed upper cap 111. The loop 109 of the second end 105 of the elastic connector 103 is sandwiched between the lower intermediate member 122 and the fixed lower cap 121.

Figure 3:
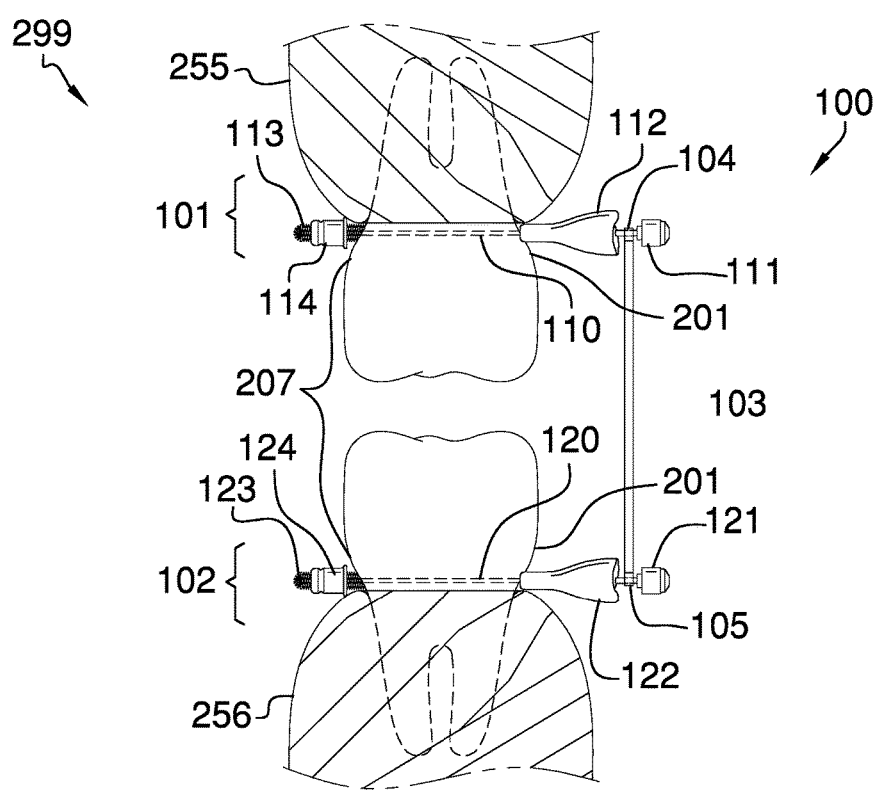
FIG. 3 is a front view of an embodiment of the disclosure in use.
Figure 4:
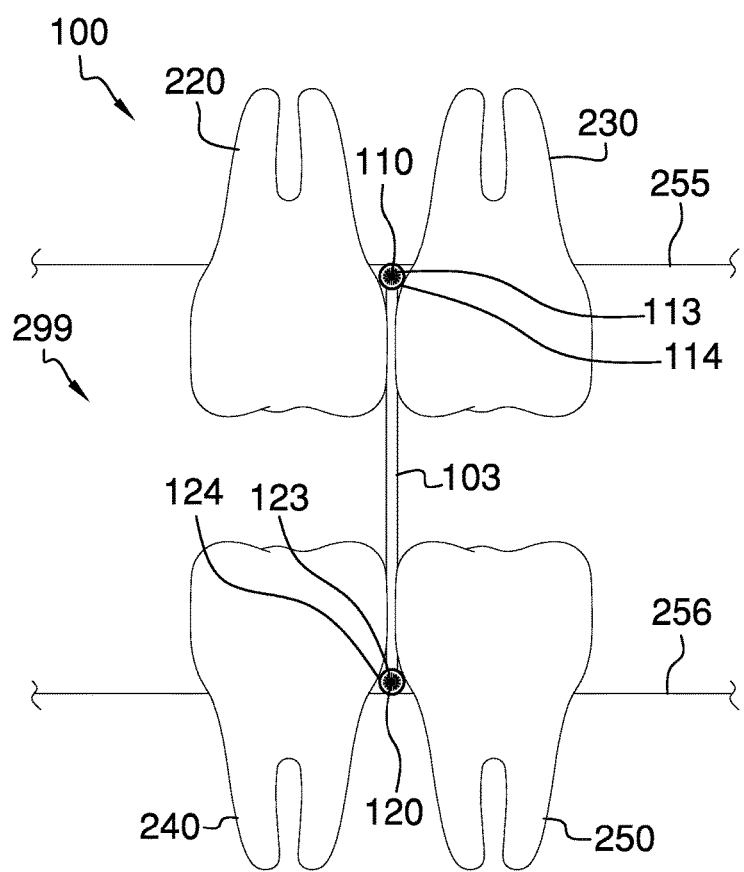
FIG. 4 is a side view of an embodiment of the disclosure in use.

Referring to FIG. 3, both the upper intermediate member 112 and the lower intermediate member 122 are polygonal-shaped objects with a tapered profile. An inner intermediate end 127 of the lower intermediate member 122 as well as the upper intermediate member 112 is adapted to interface with a facial tooth surface 201. Both the upper intermediate member 112 and the lower intermediate member 122 have an intermediate hole 128 that spans across a length 129. The intermediate hole 128 enables the upper intermediate member 112 to slide back and forth on the upper bar member 110; whereas the intermediate hole 128 enables the lower intermediate member 122 to slide back and forth on the lower bar member 120.

Both the upper bar member 110 and the lower bar member 120 have an outer diameter 130 that is less than 1 mm. Moreover, the outer diameter 130 of the upper bar member 110 and the lower bar member 120 facilitates adaptive placement between a first molar 220 and a second molar 230 (see FIG. 4). For clarity, the first molar 220 and the second molar 230 are provided on an upper mouth side 255 of a mouth 299; whereas a third molar 240 and a fourth molar 250 are provided on a lower mouth side 256 of said mouth 299.

The upper brush member 113 and the lower brush member 123 are provided at an inner end 137 of the upper bar member 110 and the lower bar member 120, respectively. The inner end 137 of the upper bar member 110 and the lower bar member 120 is opposite of where the fixed upper cap 111 and the fixed lower cap 121 are provided on the upper bar member 110 and the lower bar member 120, respectively. The upper securing cap 114 and the lower securing cap 124 are each able to slide onto the upper brush member 113 and the lower brush member 123, respectively. The upper brush member 113 and the lower brush member 123 provide resistance to secure in place the upper securing cap 114 and the lower securing cap 124.

Both the upper securing cap 114 and the lower securing cap 124 feature securing holes 177 that has an inner diameter 178 that is greater than the outer diameter 130 of the upper bar member 110 and the lower bar member 120. Moreover, the inner diameter 178 of the securing holes 177 is less than a brush outer diameter 179 of the upper brush member 113 and the lower brush member 123. The upper brush member 113 and the lower brush member 123 are each further defined with a plurality of brush bristles that move when the upper securing cap 114 and the lower securing cap 124 is placed thereon.

In use, the invention 100 provides resistance to opening a mouth 500 of an end user. The invention 100 is easily installed and removed from the mouth 500 via the upper securing cap 114 and the lower securing cap 124. The upper brush member 113 and the lower brush member 123 are adapted to interface with an inner tooth surface 207. The facial tooth surface 201 is opposite of the inner tooth surface 27. When the invention 100 is installed, the first molar 220 and the second molar 230 are sandwiched between the upper brush member 113 and the upper intermediate member 112. The same can be said for the lower brush member 123 and the lower intermediate member 122.

With respect to the above description, it is to be realized that the optimum dimensional relationship for the various components of the invention described above and in FIGS. 1 through 4, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

Is shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. An oral appliance for appetite suppression comprising:
an upper molar clip, a lower molar clip and an elastic connector;
wherein the elastic connector is positioned between the upper molar clip and the lower molar clip;
wherein the upper molar clip is adapted to be positioned between a first molar and a second molar of an upper side of said mouth;
wherein the upper molar clip is further defined with an upper bar member; wherein the upper bar member includes a fixed upper cap, an upper intermediate member, an upper brush member, and an upper securing cap
wherein the lower molar clip is adapted to be positioned between a third molar and a fourth molar of a lower side of said mouth;
wherein the lower molar clip is further defined with a lower bar member; wherein the lower bar member includes a fixed lower cap, a lower intermediate member, a lower brush member, and a lower securing cap wherein both the upper intermediate member and the lower intermediate member have an intermediate hole that spans across a length; wherein the intermediate hole enables the upper intermediate member to slide back and forth on the upper bar member; wherein the intermediate hole enables the lower intermediate member to slide back and forth on the lower bar member
wherein the elastic connector is adapted to limit the range of motion of a mouth, which prevents impulse eating.

2. The oral appliance for appetite suppression according to claim 1 wherein the elastic connector has a first end and a second end; wherein the upper molar clip is attached to the first end of the elastic connector and the lower molar clip is attached to the second end of the elastic connector.

3. The oral appliance for appetite suppression according to claim 2 wherein the upper molar clip is identical to the lower molar clip.

4. The oral appliance for appetite suppression according to claim 1 wherein the elastic connector includes a loop at the first end and at the second end.

5. The oral appliance for appetite suppression according to claim 4 wherein the loop at the first end of the elastic connector is affixed to the upper bar member; wherein the loop at the second end of the elastic connector is affixed to the lower bar member.

6. The oral appliance for appetite suppression according to claim 5 wherein the loop of the first end of the elastic connector is sandwiched between the upper intermediate member and the fixed upper cap; wherein the loop of the second end of the elastic connector is sandwiched between the lower intermediate member and the fixed lower cap.

7. The oral appliance for appetite suppression according to claim 6 wherein both the upper intermediate member and the lower intermediate member are polygonal-shaped objects with a tapered profile.

8. The oral appliance for appetite suppression according to claim 7 wherein an inner intermediate end of the lower intermediate member as well as the upper intermediate member is adapted to interface with a facial tooth surface of the first molar, the second molar, the third molar, and the fourth molar.

9. The oral appliance for appetite suppression according to claim 1 wherein both the upper bar member and the lower bar member have an outer diameter that is less than 1 mm.

10. The oral appliance for appetite suppression according to claim 9 wherein the outer diameter of the upper bar member and the lower bar member facilitates adaptive placement between the first molar and the second molar on the upper mouth side as well as between the third molar and the fourth molar on the lower mouth side.

11. The oral appliance for appetite suppression according to claim 10 wherein the upper brush member and the lower brush member are provided at an inner end of the upper bar member and the lower bar member, respectively.

12. The oral appliance for appetite suppression according to claim 11 wherein the inner end of the upper bar member and the lower bar member is opposite of where the fixed upper cap and the fixed lower cap are provided on the upper bar member and the lower bar member, respectively.

13. The oral appliance for appetite suppression according to claim 12 wherein the upper securing cap and the lower securing cap are each able to slide onto the upper brush member and the lower brush member, respectively; wherein the upper brush member and the lower brush member provide resistance to secure in place the upper securing cap and the lower securing cap.

14. The oral appliance for appetite suppression according to claim 13 wherein both the upper securing cap and the lower securing cap feature a securing hole; wherein the securing hole has an inner diameter that is greater than the outer diameter of the upper bar member and the lower bar member.

15. The oral appliance for appetite suppression according to claim 14 wherein the inner diameter of the securing hole is less than a brush outer diameter of the upper brush member and the lower brush member.

16. The oral appliance for appetite suppression according to claim 15 wherein the upper brush member and the lower brush member are each further defined with a plurality of brush bristles that move when the upper securing cap and the lower securing cap is placed thereon.

17. The oral appliance for appetite suppression according to claim 16 wherein the upper brush member and the lower brush member are adapted to interface with an inner tooth surface; wherein the facial tooth surface is opposite of the inner tooth surface; wherein the first molar and the second molar are adapted to be sandwiched between the upper brush member and the upper intermediate member; wherein the third molar and the fourth molar are adapted to be sandwiched between the lower brush member and the lower intermediate member.

\* \* \* \* \*